United States Patent [19]

Parker

[11] Patent Number: 4,463,593

[45] Date of Patent: Aug. 7, 1984

[54] APPARATUS FOR MONITORING THE PARTIAL PRESSURE OF GASES

[75] Inventor: Dawood Parker, London, England

[73] Assignee: G. D. Searle & Co., Skokie, Ill.

[21] Appl. No.: 319,003

[22] Filed: Nov. 6, 1981

[30] Foreign Application Priority Data

Nov. 11, 1980 [GB] United Kingdom ................. 8036191

[51] Int. Cl.[3] ............................................ G01N 27/54

[52] U.S. Cl. ........................................ 73/19; 204/415

[58] Field of Search .................. 73/19; 204/14, 195 P, 204/195 B, 409, 415, 432; 436/66, 178; 55/158; 128/635, 637

[56] References Cited

U.S. PATENT DOCUMENTS

| | | | |
|---|---|---|---|
| 3,418,231 | 12/1968 | Haddad | 204/195 P |
| 3,445,420 | 5/1969 | Kookootsedes et al. | |
| 3,575,836 | 4/1971 | Sternberg | 204/195 P |
| 3,661,010 | 5/1972 | Neuwelt | 73/19 |
| 3,681,032 | 8/1972 | Long | 73/19 |
| 3,767,552 | 10/1973 | Lauer | 204/195 P |
| 4,244,713 | 1/1981 | Goodwin | 73/19 |
| 4,248,712 | 2/1981 | Bauermeister | 204/195 P |
| 4,269,685 | 5/1981 | Parker | 204/415 |

FOREIGN PATENT DOCUMENTS

| | | | |
|---|---|---|---|
| 0013611 | 7/1980 | European Pat. Off. | 204/195 B |
| 902143 | 7/1962 | United Kingdom . | |
| 1143155 | 2/1969 | United Kingdom . | |
| 1387649 | 3/1975 | United Kingdom . | |
| 1494441 | 12/1977 | United Kingdom . | |
| 1512989 | 6/1978 | United Kingdom . | |
| 2027205 | 2/1980 | United Kingdom . | |
| 2041539 | 9/1980 | United Kingdom . | |

OTHER PUBLICATIONS

Dow Corning, Q7-2213, Silicone Dispersion, Bulletin: 51-419, Aug. 1977, pp. 1 and 2.

Silastic, Q7-2245, Medical Grade Elastomer, Bulletin: 51-362c, Apr. 1980, pp. 1 and 2.

*Primary Examiner*—Stephen A. Kreitman
*Attorney, Agent, or Firm*—Pollock, Vande Sande & Priddy

[57] ABSTRACT

An apparatus is disclosed for monitoring the partial pressure of a gas in the liquid flowing in a line, for example the $PO_2$ or $PCO_2$ tension in blood. The apparatus comprises a connector adapted for insertion in the line, the connector having a wall which includes a membrane permeable to the gas but impermeable to the liquid. The membrane has a first face in contact with the liquid in the connector and a second face oppositely disposed to the first face. A sensor, for example, an electrochemical sensor, is located adjacent the second face and is responsive to gas passing through the membrane from the liquid.

17 Claims, 2 Drawing Figures

APPARATUS FOR MONITORING THE PARTIAL PRESSURE OF GASES

BACKGROUND OF THE INVENTION

This invention relates to an apparatus for monitoring the partial pressure of gases, particularly in sterile liquids. One particular application of the invention, though not the only one, is for monitoring the partial pressure or tension of gases in the blood, for example the blood circulating from a heart-lung machine to a patient during open-heart surgery. In the case of blood, the tensions with which one is concerned are the oxygen tension ($PO_2$) and the carbon dioxide tension ($PCO_2$). In the case of other liquids, however, the tensions with which one may be concerned may be different.

Any system for monitoring blood gas tensions must do so without compromising the sterility of the circulating blood. This greatly influences design of electrodes for extracorporeal blood gas monitoring. Up to the present time, all electrodes designed for this purpose have been placed in direct contact with the blood, but this has a number of serious disadvantages. Firstly, the electrode must be sterile, and this imposes constraints on the electrode design. Secondly, because of the need for sterility and the need to calibrate the electrodes, it is essential that the electrodes give the same output before and after sterilization. This is difficult to achieve. Thirdly, the electrodes have to be made to be disposable after a single use, even though this is costly, because of the inconvenience and even greater cost of re-sterilization. Fourthly, once the electrode has been placed in contact with the blood it is not permissible to allow access to the electrode even if a malfunction is detected, in order to preserve the sterility of the electrode. In the event of a malfunction, therefore, useful information about the state of the blood may be lost.

SUMMARY OF THE INVENTION

According to the present invention there is provided an apparatus for monitoring the partial pressure of a gas in the liquid flowing in a line, the apparatus comprising a connector adapted for insertion in the said line, the connector having a wall which includes a membrane permeable to the said gas but impermeable to the said liquid, the membrane having a first face in contact with the said liquid in the connector and a second face oppositely disposed to the said first face, and a sensor located adjacent the said second face and responsive to gas passing through the membrane from the liquid.

The reference herein to a sensor located adjacent the said second face is intended to include the case where the actual sensing is carried out by a device, for example a mass spectrometer or gas chromatograph, located remote from the said face, and gas is fed thereto by a conduit one end of which is located adjacent the said second face.

DETAILED DESCRIPTION OF THE PREFERRED EMBODIMENTS

Figure 1:
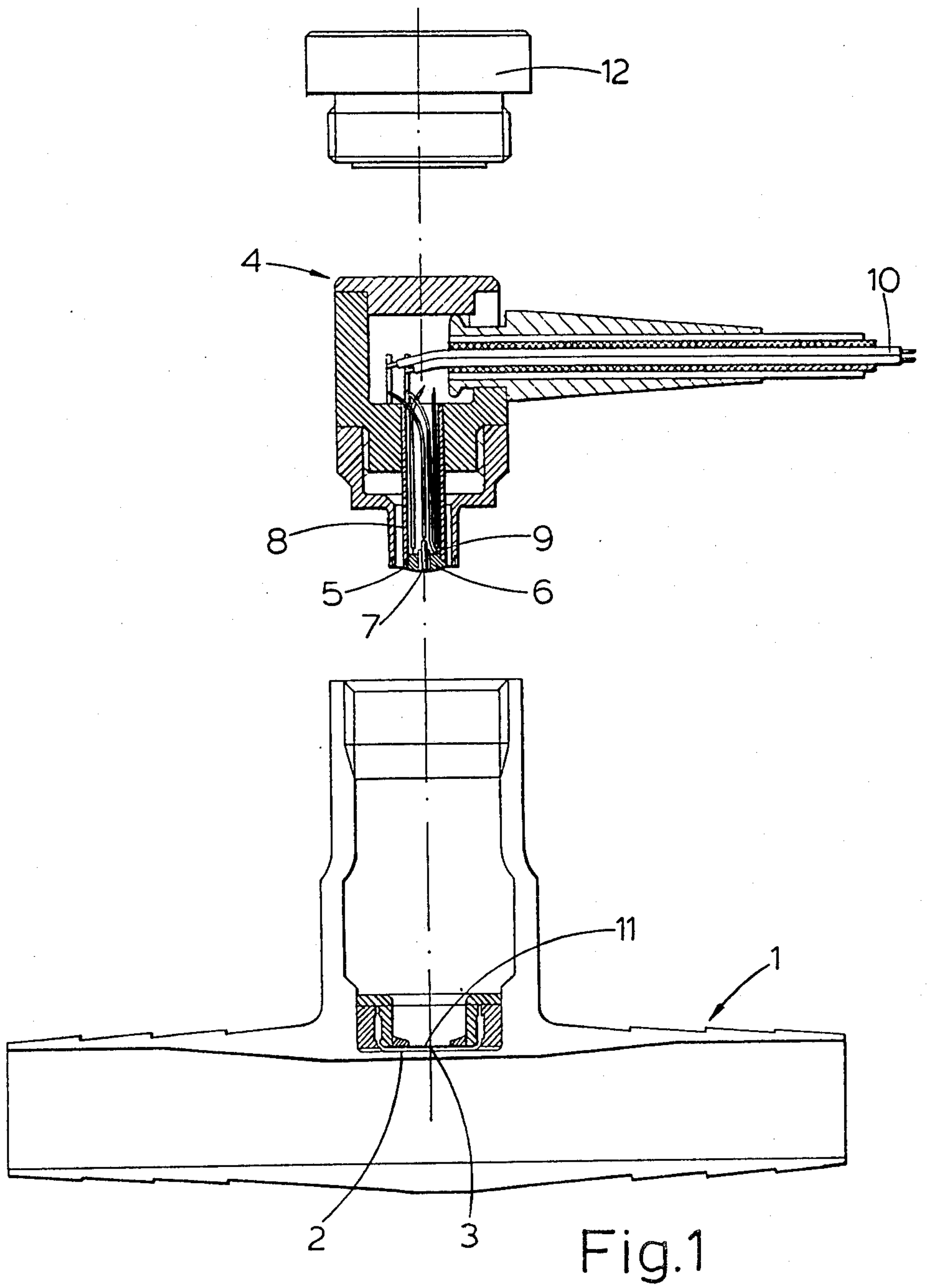
FIG. 1 is a longitudinal sectional view showing by way of example an embodiment of an apparatus according to the invention for the measurement of $PO_2$.

The apparatus shown in FIG. 1 comprises a connector 1 which is of generally T-shape. The cross-piece of the T forms two arms each of which is provided on its exterior with shoulders to enable the arms to be inserted in adjacent parts of a line in which a liquid containing the gas to be monitored is to flow. The connector is provided with an aperture which is closed by a silicone rubber membrane 2 supported by a perforated stainless steel or nickel cup 3.

The apparatus further comprises an electrochemical sensor 4. The sensor 4 may be of one of a variety of types, and the form of sensor illustrated is purely by way of example. This sensor has a polypropylene membrane 5 covering a silver anode 6 and a platinum cathode 7 which is in the form of a 25 micron diameter wire. The membrane 5 is mounted on the end of a tube 8 by means of an epoxy resin. The sensor further comprises a thermistor 9. The sensor is connected to an external measuring instrument (not shown) by means of a 4-core screened cable 10.

The connector 1 is initially supplied to a user as a sterile, disposable unit, or alternatively it may be designed to be capable of sterilization. The sensor 4 does not need to be sterile, since no part of it is in contact with liquid flowing in the connector. Before the sensor is inserted into the connector it is calibrated against the $PO_2$ in air which is generally a reliable standard (20.9% oxygen). A few drops of electrolyte are preferably placed between the membrane 2 and the membrane 5 so as to minimize the effect of oxygen leaks from the air to the electrodes of the sensor. A spacer 11 in the connector serves to maintain a predetermined spacing between the two membranes. In use, the top of the arm of the connector in which the sensor is received is sealed by a spring-loaded plug 12, which may, optionally, be made as an integral part of the sensor.

In order for the apparatus to function satisfactorily the maximum amount of oxygen per unit time which can permeate through the membrane 2 must be high compared to that of the membrane 5. Provided this condition is satisfied then, as far as the sensor 4 is concerned, the sensor will measure a $PO_2$ substantially as if it were in direct contact with the blood. Under this condition the sensor measures the $PO_2$ in the static liquid film between the two membranes, and the oxygen tension in this film is in equilibrium with the oxygen tension in the blood.

It is also necessary that the consumption of oxygen from this liquid film by the sensor should be negligible, an effect which can readily be achieved using a cathode of the dimensions mentioned above and a membrane 5 which is 12.5 to 25 microns in thickness.

Although the apparatus described above is one for use in measuring the $PO_2$ in the blood, a very similar apparatus according to the invention can be used to measure the $PCO_2$ in the blood. $PCO_2$ is most commonly measured by a potentiometric technique according to Severinghaus. In essence this is a modification of a method for determining the pH. A pH-responsive glass electrode and a reference electrode are placed in an electrolyte and covered by a carbon dioxide-permeable membrane. Carbon dioxide diffusing across the membrane in response to a $PCO_2$ difference equilibrates the internal electrolyte with the $PCO_2$ of the medium. Hydration of carbon dioxide in the electrolyte produces a carbonic acid and causes a change in hydrogen ion activity expressed by $$CO_2+H_2O=H_2CO_3=H^++HCO^-_3.$$

The pH electrode detects the alteration in $PCO_2$ as a change in pH of the electrolyte and a voltage exponentially related to $PCO_2$ results. Thus, a 10-fold increase in $PCO_2$ is approximately equivalent to a decrease of one pH unit. Since this is a potentiometric technique no carbon dioxide is consumed and the depletion effects associated with $PO_2$ electrodes do not arise. In using the Severinghaus technique in an apparatus according to the invention the same connector can be used as that described above with reference to $PO_2$ measurement. The membrane 2 then forms the diffusion membrane of the $CO_2$ sensor. A few drops of unbuffered electrolyte are placed on the membrane 2 and the $CO_2$ sensor is then completed by placing a pH electrode, which can be of known construction, in the electrolyte. In the case of $PCO_2$ monitoring, therefore, only one membrane is employed, as opposed to the two membranes used in $PO_2$ monitoring.

Figure 2:
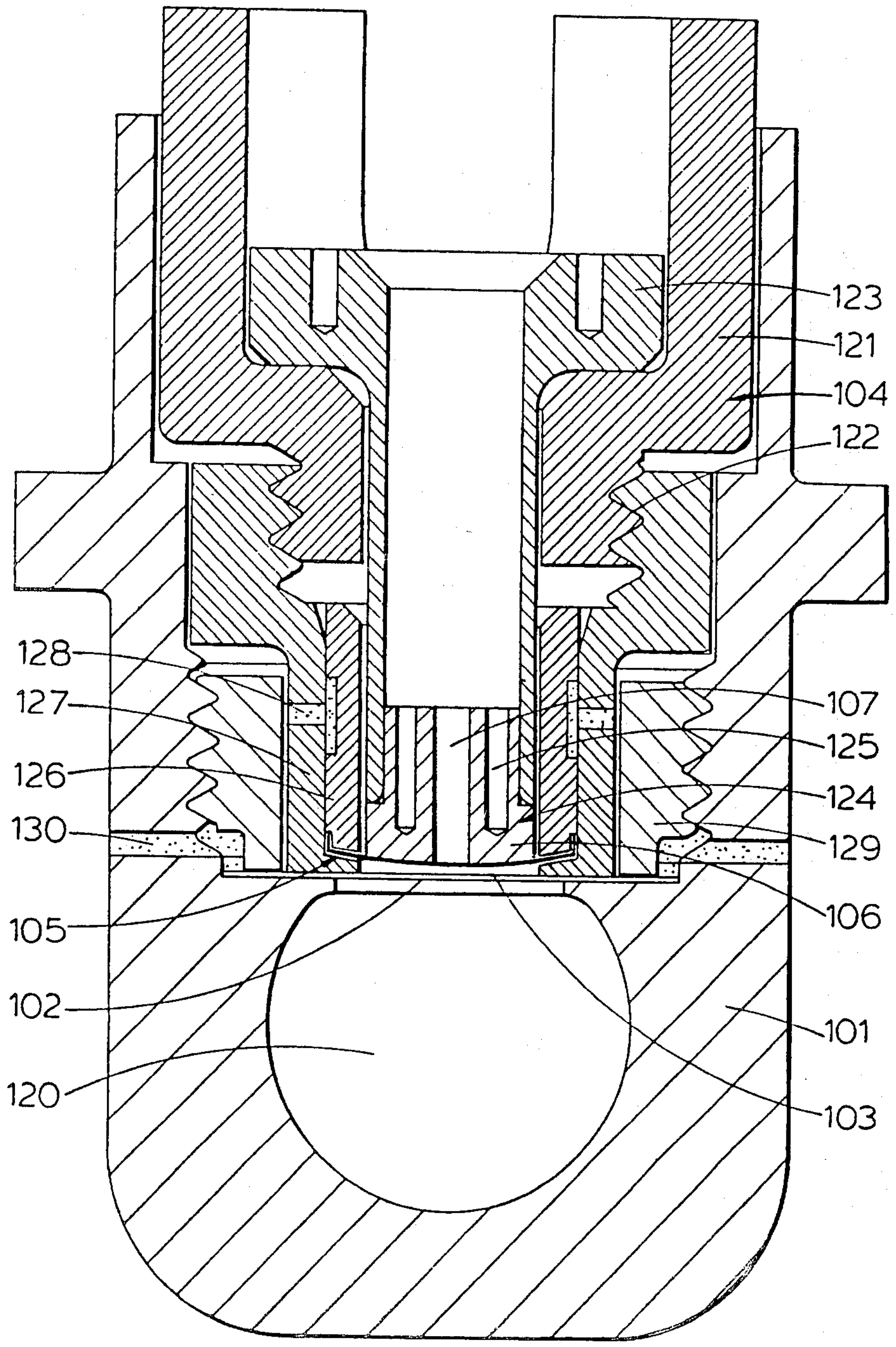
FIG. 2 is a cross-sectional view of part of another embodiment of the invention.

The embodiment of the invention, part of which is shown in FIG. 2, is, like the embodiment of FIG. 1, for the measurement of $PO_2$. In many ways the embodiment of FIG. 2 resembles that of FIG. 1, and parts in FIG. 2 which correspond to parts in FIG. 1 are denoted in FIG. 2 by the same reference numeral as in FIG. 1 with the addition of 100. Thus, the embodiment of FIG. 2 comprises a connector 101 having a passage 120 within it which is in communication with a line in which a liquid containing the gas to be monitored is to flow. The connector is provided with an aperture which is closed by a silicone rubber membrane 102 supported on a perforated nickel disc 103. The silicone rubber is solvent cast onto the nickel disk. Various types of silicone rubber may be used, for example those sold by Dow Corning Corporation as Q7-2213 (a dimethylsiloxane elastomer dispersed in 1,1,1 trichloroethane) and Q7-2245 (a 3-part system comprising a dimethylsiloxane polymer and a reinforcing silica, a polysiloxane curing agent, and an additive for inhibiting ambient temperature curing of the first two parts).

The apparatus further comprises an electro-chemical sensor 104. The sensor includes a hollow sensor body 121, the lower end of which is provided with a screw thread 122, for reasons which will become apparent from the ensuing description. Within the sensor body 121 is mounted a hollow stem 123 formed, for example, from epoxy resin. The lower end of this stem carries a sensor element 124. The element 124 includes a silver anode 106 and a platinum cathode (not shown) which extends through a cathode-receiving bore 107. The anode is also provided with a bore 125 for receiving a thermistor which detects the temperature at which the sensor element 124 is operating.

The lower end of the sensor element is closed by a sensor membrane 105. The peripheral edge of the membrane 105 is held between the parts 126 and 127 of a 2-part membrane holder body. The upper end of the part 127 has a screw thread which interlocks with the screw thread 122 provided on the sensor body 121. The two parts of the membrane holder body are held together by sealant which is present in annular recesses 128 formed in the two parts. For completeness it should be added that the component formed by the membrane 102 and disc 103 is held in place by a ring 129 which has an external thread cooperating with an internal thread on the adjacent part of the connector 101. The ring 129 is held in place in the connector 101 by sealant which is introduced into apertures 130.

It should be noted that the connector 1 or 101 is relatively cheap and can therefore be disposable, whereas the sensor 4 or 104 is relatively expensive but can be reused since it is removable from the connector.

The embodiments of the invention described above use an electro-chemical sensor. However, in a modification of the apparatus according to the invention, the electro-chemical sensor can be replaced by a purely chemical sensor, for example, a layer of crystals whose color changes in a manner which is a function of the partial pressure of some particular gas. Suitable chemical compounds for this purpose are to be found, by way of example, in a PCT patent application published under International Publication Number WO 79/00696, to which attention is directed.

While this invention is susceptible of embodiment in many different forms, there is shown in the drawings and described herein in detail the presently preferred embodiments, with the understanding the present disclosure is to be considered as an exemplification of the principles of the present invention, and is not intended to limit the invention to the embodiments illustrated. The scope of the invention is pointed out in the appended claims.

I claim:

1. An apparatus for monitoring the partial pressure of gas present in a liquid as it flows through a conduit, the apparatus comprising:

a connector for insertion in said conduit, said connector comprising:

(a) a substantially tubular passageway adapted for flow therethrough of the liquid whose partial gas pressure is to be monitored, said passageway being defined at least in part by a wall having an aperture therein, (b) a membrane having a first face for contact with liquid in said passageway and a second oppositely disposed face; said membrane being impermeable to the liquid, but permeable to the gas whose partial pressure is to be monitored;

(c) perforated support means for supporting said membrane wherein said perforated support means contacts said membrane and extends across said aperture to permit said first face thereof to be contacted by the liquid as it flows through said passageway and past said aperture therein, and (d) means for detachably receiving a removable sensor responsive to the gas that passes through said membrane from the liquid;

said apparatus also comprising a removable sensor responsive to gas passing through the membrane from the liquid;

whereby said sensor does not contact said liquid flowing in said passageway of said connector and need not be sterile; and can be removed from said connector and be reused.

2. An apparatus according to claim 1, wherein the said sensor is an electrochemical sensor.

3. An apparatus according to claim 2, wherein the said sensor has a gas permeable membrane located adjacent the membrane of the connector.

4. An apparatus according to claim 3, wherein a layer of an electrolyte is situated between, and in contact with the two membranes.

5. An apparatus according to claim 4, wherein a spacer is provided to define a predetermined spacing between the two membranes.

6. An apparatus according to any one of claims 3 to 5, wherein the said sensor is a $PO_2$ sensor.

7. An apparatus according to any one of claims 3 to 6, wherein the gas permeable membrane of the connector is formed from silicone rubber supported by a perforated metal disc.

8. An apparatus according to claim 7, wherein the silicone rubber is solvent cast onto the metal disc.

9. An apparatus according to claim 2, wherein the said sensor is a $PCO_2$ sensor.

10. An apparatus according to claim 1, wherein the sensor comprises a gas sensing means located remote from the said second face, and conduit means having a first end located adjacent the said second face and a second end communicating with the said gas sensing means.

11. An apparatus according to claim 1, wherein the connector is a T-piece formed by a cross-piece defining two arms and a third arm extending from the cross-piece, the cross-piece being adapted for insertion in the said line for liquid to flow through the cross-piece, and the membrane of the connector being located so as to block flow of liquid through the said third arm.

12. The apparatus of claim 1 which comprises means extending outward from said wall and from said membrane and surrounding said membrane for receiving and locating adjacent said second face, a removable sensor.

13. A connector for use in monitoring the partial pressure of a gas present in a liquid as it flows through a conduit and adapted for insertion into said conduit and comprising:

a substantially tubular passageway adapted for flow therethrough of the liquid whose partial gas pressure is to be monitored, said passageway being defined at least in part by a wall having an aperture therein, a membrane having a first face for contact with liquid in said passageway and a second oppositely disposed face; said membrane being impermeable to the liquid, but permeable to the gas whose partial pressure is to be monitored;

perforated support means for supporting said membrane wherein said perforated support means contacts said membrane and extends across said aperture to permit said first face thereof to be contacted by the liquid as it flows through said passageway and past said aperture therein, and means for detachably receiving a removable sensor responsive to the gas that passes through said membrane from the liquid.

14. The connector of claim 13 which comprises means extending outward from said wall and from said membrane and surrounding said membrane for receiving and locating adjacent said second face a removable sensor responsive to gas passing through the membrane from the liquid.

15. The connector of claim 13 being T-shaped and formed by a cross-piece defining two arms and a third arm extending from the cross-piece, the cross-piece being adapted for insertion in the said line for liquid to flow through the cross-piece, and the membrane of the connector being located so as to block flow of liquid through the said third arm.

16. The connector of claim 13 wherein the gas permeable membrane is formed from silicone rubber supported by a perforated metal disc.

17. The connector of claim 16, wherein the silicone rubber is solvent cast onto the metal disc.

* * * * *